April 18, 1933. C. E. SCHUSTER Plant Pat. 60
STRAWBERRY
Filed May 19, 1931
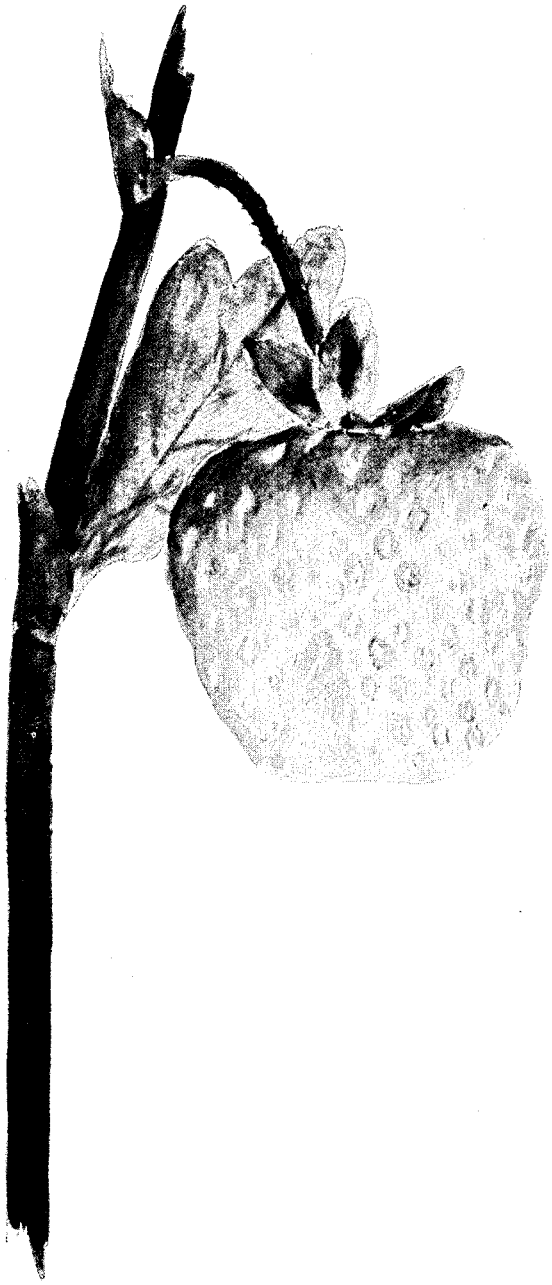
Inventor:
Carl E. Schuster
By: G. Meinkheim
Attorney.

Patented Apr. 18, 1933

Plant Pat. 60

UNITED STATES PATENT OFFICE

CARL E. SCHUSTER, OF CORVALLIS, OREGON, DEDICATED, BY MESNE ASSIGNMENTS, TO THE PEOPLE OF THE UNITED STATES OF AMERICA

STRAWBERRY

Application filed May 19, 1931. Serial No. 538,467.

(GRANTED UNDER THE ACT OF MARCH 3, 1883, AS AMENDED APRIL 30, 1928; 370 O. G. 757)

This application is made under the act of May 23, 1930 and the act of March 3, 1883, as amended by the act of April 30, 1928, and the discovery herein described may be used by the Government or any of its officers or employees in the prosecution of work for the Government, and by any person in the United States, either in public or private work, without the payment to me of any royalty thereon.

This discovery relates to a strawberry grown by me from seed and then vegetatively propagated. This strawberry is a cross or hybrid between the Ettersburg #121 and the Marshall strawberry.

Its plants are large, vigorous, upright, with close-growing foliage. It is more vigorous than the Marshall, equally as vigorous as the Ettersburg #121. Its leaves are large, greenish-yellow, very resistant to leaf spot, more so than either the Marshall or the Ettersburg #121. Pubescence is light, spreading. The fruit stalks are heavy, much branched, fairly erect, holding the fruit off the ground in good shape. The flowers are medium sized, perfect, setting fruit to the last flower or terminal flower.

The fruit has a blunt conic to oblate form, with no neck. It is medium sized. Pubescence on the pedicels is spreading. The calyx of the larger early berries is reflexed; of the smaller later berries sometimes slightly reflexed. The apex and all sides ripen uniformly. The surface is glossy and luminous. The color is bright crimson. The seeds are yellow and red, sunken. The flesh is crimson. Texture is firm to melting, juicy and very smooth. There is little trace of a core. The skin is tender. Taste is acid, aromatic. Dessert quality is very high. The fruit is excellent for canning. It is well adapted to freezing trade and to the fresh trade. The season is late, about with the Ettersburg #121.

This new variety of strawberry has a canning quality equal to that of Ettersburg #121, but is adapted to other soils on which Ettersburg #121 will not grow.

Like the Marshall, this strawberry has a quality suitable for the frozen pack trade and is also adapted to the fresh market trade, coming on the market after the Marshall and not in competition with any other variety. Its quality is similar to that of the Marshall, but the berry is more acid and more aromatic than Ettersburg #121.

Another characteristic quality of this strawberry is that it contains acidity to the extent that it is considered an acid berry. I have discovered that the outstanding feature of this strawberry is its canning quality, and its adaptability to a wide range of soils, with a quality suitable for the frozen pack trade; and, as a fresh market berry following the Marshall.

I have discovered that my new variety of strawberry is adapted to the fresh market trade, but is later than any other strawberry now in use for that trade.

The foregoing description of the characteristics of this variety apply to conditions existing in the Willamette Valley during the period in which this variety was under test, and I do not wish to be restricted to these descriptions when the variety is grown under conditions not similar to those under which the berry has been tested.

Having thus fully and clearly described my discovery, what I claim as new and desire to secure by Letters Patent is:

A strawberry plant, as described, bearing fruit characterized by being medium in size, conic to oblate in form, with no neck, the calyx on the larger, early berries reflexed when ripe; having a uniform ripening quality; having a surface glossy and luminous, and bright crimson in color; having seeds that are sunken yellow red; having flesh crimson in color, the texture being firm to melting, very smooth, with little trace of core; and having excellent canning and dessert quality, acid and aromatic, adapted to the frozen and late fresh market trade, as shown.

CARL E. SCHUSTER.